United States Patent [19]

Lohmann et al.

[11] Patent Number: 5,708,152
[45] Date of Patent: Jan. 13, 1998

[54] N-SUBSTITUTED CHITOSAN DERIVATIVES IN A PROCESS FOR THEIR PREPARATION

[75] Inventors: Dieter Lohmann, Münchenstein, Switzerland; Donald Richard Randell, Stockport, England

[73] Assignee: Ciba Specialty Chemicals Corporation, Tarrytown, N.Y.

[21] Appl. No.: 451,324

[22] Filed: May 26, 1995

Related U.S. Application Data

[63] Continuation-in-part of Ser. No. 36,635, Mar. 24, 1993, abandoned.

[30] Foreign Application Priority Data

Mar. 27, 1992 [CH] Switzerland ............... 981/92

[51] Int. Cl.⁶ ............................ C08B 37/08
[52] U.S. Cl. ....................... 536/20; 536/124
[58] Field of Search ..................... 536/20, 124

[56] References Cited

U.S. PATENT DOCUMENTS

| | | | |
|---|---|---|---|
| 3,879,376 | 4/1975 | Vanderberghe et al. | 536/20 |
| 3,953,608 | 4/1976 | Vanderberghe et al. | 514/777 |
| 4,031,025 | 6/1977 | Vanderberghe et al. | 252/180 |

FOREIGN PATENT DOCUMENTS

| | | |
|---|---|---|
| 2222733 | 11/1972 | Germany . |
| 3432227 | 3/1986 | Germany . |
| 0419529 | 3/1974 | U.S.S.R. . |

OTHER PUBLICATIONS

CA 104(24):209102v of DE 3,432,227 (1986).
Kurita et al.; Polymer Journal, vol. 22, No. 5, pp. 429–434 (1990).
E. Loubaki et al., Eur. Polym. J., vol. 25, No. 4, pp. 379–384 (1989).
Chem. Abst., vol. 82, #8 (1975) 45565x.
Derwent Publi., 28468f & 05216w, of SU 419529, (1974).
Chemical Abst., vol. 67, #9 (1967) 43395h.

*Primary Examiner*—Kathleen K. Fonda
*Attorney, Agent, or Firm*—Kevin T. Mansfield

[57] ABSTRACT

Chitosan derivatives having structural units of formula I, II and III in random distribution

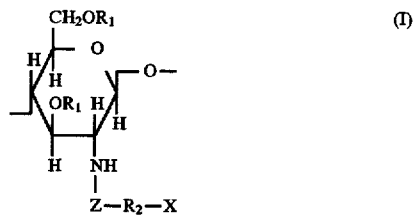

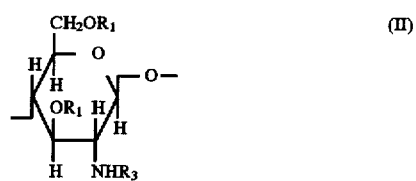

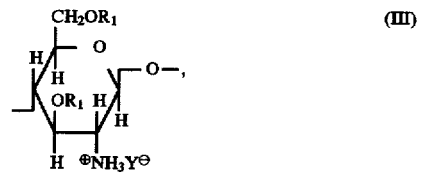

wherein the substituents $R_1$ are each, independently of one another, H or $-Z-R_2-X$, $R_3$ is H or acetyl, Y is the anion $O-Z-R_2-X$, and (a) Z is $-CO-$ or $-SO_2-$, X is $-CO_2H$, $-CH_2CO_2H$ or $-CH_2PO(OH)_2$, and $R_2$ is $-CHR_4CR_5(OH)-$, $R_4$ is $-H$, $-OH$, $C_1-C_4$alkoxy or $C_1-C_4$alkyl, and $R_5$ is H or $C_1-C_4$alkyl, or (b) Z is $-CO-$, X is $-CO_2H$, and $R_2$ is $-CHR_6-CHR_7-CH(OH)-$ or $-CHR_8-CHR_9-CHR_{10}-CH(OH)-$, $R_6$, $R_7$, $R_8$ and $R_{10}$ are each, independently of one another, $-H$, $-OH$, $C_1-C_4$alkyl or $C_1-C_4$alkoxy, and $R_9$ is $-H$, $-OH$, $C_1-C_4$alkyl, $C_1-C_4$alkoxy or $-CO_2H$, and the esters and salts thereof, which chitosan derivative contains a total of at least 2 structural units and, based on 1 mol of the chitosan derivative, 30 to 100% molar of structural units of formula I, 60 to 0% molar of structural units of formula II, and 30 to 0% molar of structural units of formula III, and the sum of the molar percentages is 100%. These derivatives are suitable for use as humectants and for the prevention of the adherence to and/or formation of solid deposits on inorganic or organic substrates.

14 Claims, No Drawings

N-SUBSTITUTED CHITOSAN DERIVATIVES IN A PROCESS FOR THEIR PREPARATION

CROSS-REFERENCE TO RELATED APPLICATION

This application is a continuation-in-part of application Ser. No. 08/036,635, filed Mar. 24, 1993 now abandoned.

The present invention relates to chitosan derivatives the amino groups of which are substituted by hydroxyacyl that carries a carboxylic acid, phosphonic acid or sulfonic acid group, or the esters and salts thereof, to a process for their preparation by reacting a chitosan with a 4- or 6-membered lactone or a 4-membered sultone that carries sulfonic acid ester, phosphonic acid ester or carboxylic acid ester or $CCl_3$ groups, and subsequently hydrolysing $CCl_3$ groups, if desired converting ester groups into acid groups and acid groups thereafter into salts, and to the use thereof for preventing the adherence to and/or formation of solid coats on inorganic or organic substrates, as well as to the use thereof as humectants for skin and mucous membranes.

Chitosan derivatives which carry carboxyalkyl-substituted amino groups are disclosed in U.S. Pat. No. 3,953,608. They are prepared by reacting three defined monomers, in the respective ratios of 30-90:5-30:5-40, with a cyclic anhydride such as succinic anhydride. There is no enabling disclosure of hydroxyl-substituted cyclic anhydride reactants in U.S. Pat. No. 3,953,608 which reactants, indeed, are unknown in the literature. Moreover, hydroxyl-substituted anhydride reactants are excluded in the description in U.S. Pat. No. 3,953,608 of the synthesis of the disclosed chitosan derivatives. The disclosed chitosan derivatives may be used as chelating agents, detergents, and as additives for cosmetic or pharmaceutical compositions.

Sulfopropyl derivatives of chitosan that are obtained by reacting chitosan with 1,3-propanesultone are disclosed in DE-A-3 432 227. These derivatives are used as additives for cosmetic compositions.

K. Kurita et al., in Polymer Journal 22, No. 5, pages 429–434 (1990), describe the reaction of chitosan with γ-butyrolactone to prepare γ-hydroxybutanoyl-substituted chitosan derivatives. E. Loubaki et al. in Eur. Polym. J, 25, No. 4, pages 379–84 (1989) describe a similar modification of chitosan with β-propiolactone and δ-gluconolactone.

Chitosan derivatives, the N-substituent of which carries hydroxyl groups and acid groups, and which are thereby capable of salt formation, are not yet known in the art. It has now been found that such chitosan derivatives are obtained in good yield and quality by using, instead of inert lactones, those carrying an activating group in α-position to the ring oxygen atom. The new chitosan derivatives are suitable as substitutes for hyaluronic acid for many utilities.

In one of its aspects, the invention relates to oligomeric and polymeric chitosan derivatives containing structural units of formulae I, II and III in random distribution

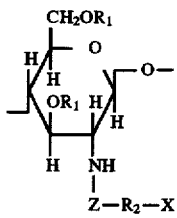
(I)

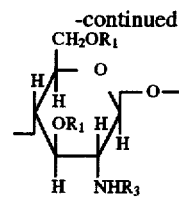
(II)

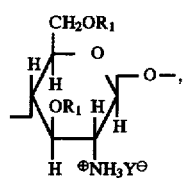
(III)

wherein the substituents $R_1$ are each, independently of one another, H or the radical —Z—$R_2$—X, $R_3$ is H or acetyl, Y is the anion O—Z—$R_2$—X, and (a) Z is —CO— or —$SO_2$—, X is —$CO_2H$, —$CH_2CO_2H$ or —$CH_2PO(OH)_2$, and $R_2$ is —$CHR_4CR_5(OH)$—, $R_4$ is —H, —OH, $C_1$-$C_4$alkoxy or $C_1$-$C_4$alkyl, and $R_5$ is H or $C_1$-$C_4$alkyl, or (b) Z is —CO—, X is —$CO_2H$, and $R_2$ is —$CHR_6$—$CHR_7$—CH(OH)— or —$CHR_8$—$CHR_9$—$CHR_{10}$—CH(OH)—, $R_6$, $R_7$, $R_8$ and $R_{10}$ are each, independently of one another, —H, —OH, $C_1$-$C_4$alkyl or $C_1$-$C_4$alkoxy, and $R_9$ is —H, —OH, $C_1$-$C_4$alkyl, $C_1$-$C_4$alkoxy or —$CO_2H$, and the esters and salts thereof, which chitosan derivatives contain a total of at least 2 structural units and, based on 1 mol of the chitosan derivative, 30 to 100% molar of structural units of formula I, 60 to 0% molar of structural units of formula II, and 30 to 0% molar of structural units of formula III, and the sum of the molar percentages is 100%.

In preferred embodiment of the invention, the chitosan derivative contains a total of at least 4 structural units, oligomers preferably containing 4 to 50, most preferably 6 to 30, structural units. Polymeric chitosan derivatives may typically contain up to 10 000, preferably up to 8000 and, most preferably, up to 5000, structural units.

In a further preferred embodiment of the invention, the chitosan derivative contains 50 to 100% molar of structural units of formula I, 50 to 0% molar of structural units of formula II, and 20 to 0% molar of structural units of formula III, the sum of the molar percentages being 100%. Most preferably, the chitosan derivative contains 60 to 100% molar of structural units of formula I, 40 to 0% molar of structural units of formula II, and 10 to 0% molar of structural units of formula III, the sum of the molar percentages being 100%.

Z in definition (a) of the structural units I, II and III is preferably —CO— and X is preferably —$CO_2H$ or —$CH_2PO(OH)_2$, or Z is —$SO_2$— and X is —$CO_2H$.

$R_4$ to $R_{10}$ as alkyl may be methyl, ethyl, n- or isopropyl or n-, iso- or tert-butyl. Preferably $R_4$ to $R_{10}$ as alkyl are methyl or ethyl.

$R_4$ to $R_{10}$ as alkoxy may be methoxy, ethoxy, propoxy or butoxy. Preferably $R_4$ to $R_{10}$ as alkoxy are methoxy.

$R_4$ and $R_6$ to $R_{10}$ are preferably H, OH, methyl or methoxy and $R_5$ is H or methyl.

Typical examples of $R_2$ are —$CH_2CH(OH)$—, —$CH_2C(CH_3)(OH)$—, —CH(OH)CH(OH)—, —$CH(CH_3)CH(OH)$—, —$CH(OCH_3)CH(OH)$—, —$CH_2CH_2CH(OH)$—, —CH(OH)$CH_2CH(OH)$—, —CH(OH)CH(OH)CH(OH)—, —$CH(CH_3)CH_2CH(OH)$—, —$CH_2CH(OH)CH(OH)$—, —$CH(OCH_3)CH(OH)CH(OH)$—, —$CH_2CH(OCH_3)$CH (OH)—, —CH₂CH₂CH₂CH(OH)—, —CH₂CH₂CH(OH)CH(OH)—, —CH₂CH(OH)CH(OH)CH(OH)—, —CH₂CH(COOH)CH₂CH(OH)—, —CH₂CH(OH)CH(CH₃)CH(OH)— and —CH₂CH(OH)CH(OCH₃)CH(OH)—. Most preferably R₂ is —CH₂CH(OH)— and —CH₂C(CH₃)(OH)—.

The carboxylic acid and phosphonic acid group can be esterified, typically with an aliphatic, cycloaliphatic, araliphatic or aromatic alcohol which contains 1 to 30, 1 to 20 and, most preferably, 1 to 12, carbon atoms. Representative examples of such alcohols are alkanols such as methanol, ethanol, propanol, butanol, pentanol, hexanol, heptanol, octanol, nonanol, decanol, undecanol, dodecanol, tetradecanol, octadecanol; polyoxaalkanols such as ethylene glycol monomethyl ether or monoethyl ether, diethylene monomethyl ether or monoethyl ether, oligoethylene glycols or oligopropylene glycols or copolymers thereof containing a total of up to 20, preferably of up to 12, monomer units; cycloalkanols such as cyclopentanol and cyclohexanol; benzyl alcohol and $C_1$-$C_{12}$alkyl-substituted benzyl alcohols; phenol and $C_1$-$C_{12}$alkyl-substituted phenols.

The carboxylic acid and phosphonic acid groups may also be in salt form. They may be metals of the main and subsidiary groups of the Periodic System of the elements, typically the metals of the third, fourth and fifth main group and the subsidiary groups of the Periodic System of the chemical elements. Particularly suitable metals are Li, Na, K, Mg, Ca, Sr, Ba, B, Al, Ca, In, Sn, Pb, Sb, Bi, Cu, Ag, Au, Zn, Cd, Hg, So, Y, La, Ti, Zr, Hf, V, Nb, Ta, Cr, Mo, W, Fe, Co, Ni, Ru, Rh, Pd, Os, Ir, Pt and the lanthanide metals Ce, Pr, Nd, Pro, Sm, Eu, Gd, Th, Dy, Ho, Er, Tm, Yb and Lu. When using polyvalent metals, the corresponding cations can act as crosslinkers of the oligomer and polymer chains. Preferred metals are the alkali metals and alkaline earth metals. The salts may also be in the form of amine salts, conveniently of ammonium salts or salts of primary, secondary or tertiary amines which preferably contain 1 to 20 and, most preferably, 1 to 12, carbon atoms, or of salts of polyamines containing primary, secondary and/or tertiary amino groups and, preferably, 2 to 20, most preferably, 2 to 16, carbon atoms, or of salts of a polymer containing amino groups in structural repeating units.

Typical examples of amines are: methylamine, dimethylamine, trimethylamine, ethylamine, diethylamine, triethylamine, n-propylamine, isopropylamine, di-n-propylamine, diisopropylamine, tri-n-propylamine, triisopropylamine, n-butylamine, di-n-butylamine, tri-n-butylamine, hexylamine, dodecylamine, octadecylamine, icosylamine, morpholine, N-methylmorpholine, piperidine, N-methylpiperidine, aniline, N-methylaniline, N-dimethylaniline, pyridine, pyrimidine, ethanolamine, diethanolamine and triethanolamine.

Typical examples of polyamines are: ethylenediamine, N,N'-dimethylethylenediamine, diethylenetriamine, triethylenetetramine, 1,3-diaminopropane, 1,3-dimethylaminopropane, 1,4-diaminobutane, piperazine, phenylenediamine, naphthylenediamine, 4,4'-diaminodiphenyl, 4,4'-diaminodiphenyl ether, 4,4'-diaminodiphenyl thioether 4,4'-diaminodiphenylmethane.

Typical examples of polymers containing amino groups are poly(aminosaccharides) such as chitosan itself and polygalactosamine, albumin or polyethylenimine, low molecular polyamides carrying amino end groups and aminoalkylated polyacrylamides or polymethacrylamides.

The chitosan derivatives can be prepared in simple manner by reacting chitosan with β-, γ- or δ-lactones or β-sultones which contain an esterified carboxyl group or a $CCl_3$ group in α-position to the ring oxygen atom, and subsequently hydrolysing the $CCl_3$ group and, if desired, converting the ester groups into acid groups and the acid groups into salts.

In another of its aspects, the invention relates to a process for the preparation of the novel chitosan derivatives containing a total of at least 2 structural units of formulae I, II and III in random distribution, which process comprises reacting a chitosan containing a total of at least 2 structural units of formulae IV and V in random distribution,

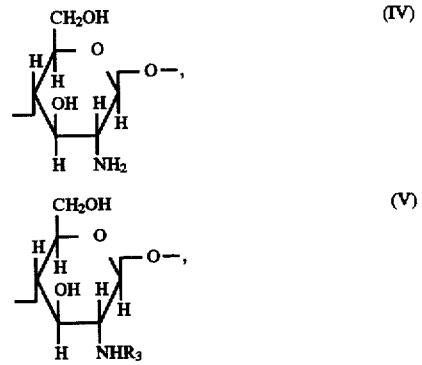

wherein $R_3$ is acetyl or H, and said chitosan contains 30 to 100% molar of structural units of formula IV and 70 to 0% molar of structural units of formula V, based on 1 mol of chitosan, in the presence of an inert solvent, with at least 30% molar of a lactone of formula VI, VII or VIII, based on said chitosan,

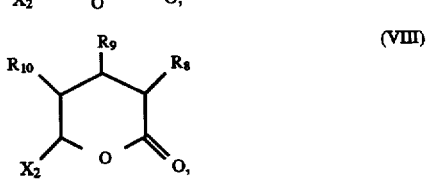

wherein $R_4$, $R_5$, $R_6$, $R_7$, $R_8$, $R_9$ and $R_{10}$ have the meanings previously assigned to them, $Z_1$ is =CO or =SO₂, $X_1$ is —CCl₃, —CO₂R₁₁, —CH₂CO₂R₁₁ or —CH₂PO(OR₁₁)₂, $X_2$ is —CO₂R₁₁, and $R_{11}$ is the radical of an alcohol of 1 to 20 carbon atoms which lacks the hydroxyl group, and hydrolysing the resultant chitosan derivatives, wherein $X_1$ is —CCl₃, under alkaline conditions to form the corresponding carboxylic acid salts, if desired converting the carboxylic acid salts and esters into the corresponding acids and the acids into salts. By adjusting the pH of the reaction mixture, the carboxylic acid salts can be converted into the corresponding acids, which are also isolated as such.

Surprisingly, the inventive process makes it possible for the first time to prepare N-acylated chitosans containing acid and hydroxyl groups in the N-acyl group. Particularly advantageous is the use of the β-lactones and β-sultones which contain CCl₃ groups, as these CCl₃ groups can be converted in simple manner into the carboxyl group. The reaction leads under mild conditions to high chemical conversions such that even complete substitutions at the NH₂ group of the chitosan can be achieved and side-reactions substantially avoided.

In yet another of its aspects, the invention relates to the intermediate chitosan derivatives containing structural units of formulae IX and X in random distribution,

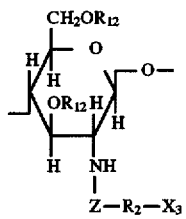

(IX)

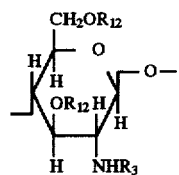

(X)

wherein the $R_{12}$ substituents are each independently of the other H or the radical —$Z$—$R_2$—$X_3$, $R_3$ is H or acetyl, Z is —CO— or —$SO_2$—, $X_3$ is —$CCl_3$, and $R_2$ is —$CHR_4CR_5$(OH)—, $R_4$ is —H, —OH, $C_1$-$C_4$alkoxy or $C_1$-$C_4$alkyl, and $R_5$ is H or $C_1$-$C_4$alkyl, which chitosan derivative contains a total of at least 2 structural units and, based on 1 mol of said chitosan derivative, 30 to 100% molar of structural units of formula IX and 70 to 0% molar of structural units of formula X.

$R_{12}$ is preferably H, and $X_3$ is preferably —$CCl_3$. Z is preferably —CO—. $R_2$, $R_4$ and $R_5$ have the preferred meanings previously assigned to them. Most preferably $R_2$ represents the radicals —$CH_2CH(OH)$— and $CH_2C(CH_3)(OH)$—. With respect to the number of structural units and the content of structural units, reference is made to the preferences stated previously concerning the novel chitosan acids, esters and acid salts.

It has been found useful to activate the commercially available chitosan before the reaction by dissolving the chitosan in e.g. dilute acetic acid, removing undissolved constituents by filtration and then neutralising with a dilute aqueous base, conveniently NaOH, until the pH is c. 8–9, so that the chitosan again precipitates. The salts are removed by known methods, typically by washing off or dialysis. The product can then be hyroextracted by repeated centrifugation with a non-solvent, conveniently an ether such as dioxane, to give products with water contents of c. 3 to 10% by weight which are highly swollen and have a high reactivity. Depending on the reaction conditions and on the water content of the chitosan used, it is possible during the reaction by hydrolysis to obtain hydroxycarboxylic acids which lead to chitosan derivatives containing structural units of formula III by salt formation. The reaction can, however, be completely suppressed by mild conditions, so that it is also possible to obtain chitosan derivatives which do not contain structural units of formula III. Under drastic reaction conditions, and given a high water and acetyl group content of the chitosan, it is possible to obtain highly swellable gels as final products which are readily crosslinked.

In the course of the reaction a limited reaction of the free hydroxyl groups with the lactones can also take place; but this reaction can be substantially suppressed by the choice of reaction conditions. Chitosan derivatives wherein $R_1$ is hydrogen in the structural units of formulae I, II and III are preferred.

The amount of structural units of formula II will depend on the one hand on the content of acetyl groups in the chitosan and, on the other, on the reactivity of the lactones used and on the degree of substitution which is attainable. Commercially available chitosans can contain up to 70% molar of acetyl group containing structural units of formula V.

Oligomeric chitosans can be typically obtained by hydrolytic degradation of the polymers, for example with a dilute mineral acid such as hydrochloric acid. The mixtures of oligomers obtained are then neutralised with e.g. NaOH and freed from salts and low molecular constituents by ultrafiltration through a membrane. The resultant mixtures of oligomers can be used as obtained or fractionated beforehand in known manner. Oligomeric chitosans can also be obtained by deacetylation of chitosan oligomers, for example deacetylated chitobiose or chitohexaose, which are also commercially available.

The lactones suitable for use in the practice of this invention are known, some being commercially available or obtainable by known methods.

The inventive process may be carried out by dissolving or suspending the chitosan in a solvent and then adding the solution or suspension to a solution of the lactone. This step is preferably carried out at room temperature. Afterwards, the reaction mixture is stirred at room or elevated temperature and the reaction is allowed to go to completion. The reaction can be carried out in the temperature range from 0° to 150° C., preferably from 10° to 120° C. and, most preferably, from 20° to 100° C.

The reaction is conveniently carried out excluding moisture, for example humidity or water in solvents. In general, the process is conveniently carried out in a dry inert gas atmosphere, typically a rare gas (helium or argon) or nitrogen.

Suitable solvents are typically polar aprotic solvents which can be used singly or as mixtures of at least two or more solvents and in which are the chitosan dissolves or swells. The solvents can also be used as suspension agents. Exemplary of such solvents are ethers (dibutyl ether, tetrahydrofuran, dioxane, ethylene glycol dimethyl ether, ethylene glycol diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), N-alkylated carboxamides and lactams (N,N-dimethylformamide, N,N-diethylformamide, N,N-dimethylacetamide, tetramethylurea, hexamethylphosphoric triamide, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), substituted benzenes (benzonitrile, chlorobenzene, o-dichlorobenzene, 1,2,4-trichlorobenzene, nitrobenzene), nitriles (acetonitrile, propionitrile). Also suitable are aromatic-aliphatic ethers such as methyl or ethyl phenyl ether, and ketones such as acetone, methyl ethyl ketone, methyl propyl ketone, dipropyl ketone, dibutyl ketone and methyl isobutyl ketone.

A group of preferred solvents comprises cyclic ethers, N-alkylated acid amides and lactams, sulfoxides and sulfones.

The reaction products can be isolated and purified either by known processes or subsequently hydrolysed directly and/or converted into salts.

The reaction products containing $CCl_3$ groups are conveniently hydrolysed with aqueous alkali metal bases, typically KOH or NaOH, and, depending on the adjustment of the pH after the reaction, the acids or their sodium or potassium salts can be isolated in per se known manner.

The novel esters can likewise, as described above, be hydrolysed with aqueous alkali metal bases to the acids or converted into the salts. Novel esters, for example benzyl ester, can also be convened catalytically with hydrogen in the presence of a noble metal catalyst into the desired carboxylic acids. It is further possible to convert the ester group into a readily hydrolysable group, for example with trimethylbromosilane, and then to remove this group by hydrolysis to form carboxylic acid groups.

The preparation of salts from the novel chitosan acids or their alkali metal salts can be carried out in per se known manner by reaction with metal salts of e.g. mineral acids or carboxylic acids in aqueous solution, in which case—especially when using polyvalent metal salts—the chitosan salts form insoluble polyelectrolyte gels. Suitable metals are those previously cited. Suitable metal salts are typically oxides, hydroxides, fluorides, chlorides, bromides, sulfates, nitrites, nitrates, phosphites, phosphates, formates and acetates.

The preparation of salts from the novel chitosan acids and ammonia, mono- or polyamines or polymeric polyamines can be carried out in the same manner. Water-insoluble polyelectrolyte gels are also obtained when using polyamines or polymeric polyamines.

The novel chitosan derivatives can be isolated by known methods, typically filtration, whereas soluble products can be precipitated beforehand by addition of non-solvents or by adjusting the pH. The products can be isolated by dialysis or by passage over ion exchange resins. For purification, the products can be washed and then dried, but without a complete drying being necessary, and the purified products may have water contents of up to c. 40% by weight and more. The products can also be milled to powders. Lyophilisation is particularly useful, as bulky and cottonwool-like products are obtained which are especially readily soluble and very reactive.

The novel chitosan derivatives are solid products which are readily soluble or highly swellable in aqueous or aqueous-alkaline media or in polar organic solvents. The free acids or their salts with non-toxic cations are physiologically acceptable and biodegradable. The products are suitable for a wide range of utilities.

The novel chitosan derivatives, especially the salts and acids, are polyampholytes with film-forming and chelating properties also in the presence of alkaline earth metal ions. Owing to their pronounced chelating action for heavy metal ions even in low concentrations, the products can be used for removing such cations from contaminated water, for example for removing iron or copper ions from mains water. In addition, they can be used as chelating agents in the food industry, the pharmaceutical industry and the textile industry, as well as detergents singly or in conjunction with cationic, anionic or neutral detergents.

The novel chitosan derivatives have a surprisingly good complexing action for metal ions, whereby the precipitation of polymeric metal salts, especially in the case of polyvalent cations, can be favourably influenced or prevented. Furthermore, they have a modulating action in crystallisation processes, especially on the formation of seed crystals, their growth and the morphology of the resultant crystals and their size distributions, as well as on the aggregation and adhesion properties. They are therefore suitable for water treatment to prevent the formation of deposits in water-conducting systems (water treatment plants), for example on the walls of containers, membranes or conduits. They can also be used for the pretreatment of textiles, conveniently cotton. The novel chitosan derivatives also prevent the formation of deposits of inorganic and/or organic components. They are therefore also suitable for use as additives for dental care products for the prevention of dental plaque, as well as additives for detergent formulations.

The invention further relates to a process for the prevention of the adherence to and/or formation of solid deposits on inorganic or organic substrates, which comprises adding to a fluid or a composition that is in contact with an inorganic or organic substrate at least one of the novel chitosans, but preferably 0.01 to 20% by weight, most preferably 0.1 to 10% by weight.

The novel chitosan derivatives have film-forming properties. The evaporation of aqueous solutions leads to the formation of transparent, solid and water-containing films which are permeable to air and moisture. By virtue of this property and their hydropectic action, they are also suitable for use as humectants for the skin or mucous membranes in cosmetic and pharmaceutical compositions, as agents for maintaining articular mobility (lubricant action simlar to that of hyaluronic acid), and for surgical dressings. Typical cosmetic formulations are skin and hair care products and deodorants. The novel chitosan derivatives, especially gels made therefrom and also the esters, are further suitable for the preparation of compositions with controlled release of the chemical agent over a prolonged period.

The novel chitosan derivatives also have a viscosity increasing and dispersing action in aqueous solutions. They are thus suitable for use as additives in suspensions, emulsions and aqueous solutions, for example in the manufacture of foodstuffs or active substance concentrations as well as in dye and pigment formulations.

The novel chitosan derivatives can also have biocidal activity, typically bacteriostatic, fungistatic or algicidic activity.

Especially preferred, and a further object of the invention, is the use of the novel chitosan derivatives, preferably the acids or alkali metal salts, for preventing the adhesion to and/or formation of solid deposits on inorganic or organic substrates. The deposits, which often have a crusty consistency, may be composed of inorganic and/or organic components, typically salts and polymers, also of biological origin. The substrates may be inorganic and/or organic materials or biological materials, for example glass, ceramics, metals and alloys, natural or synthetic plastic materials, paper, textiles, leather or vegetable or animal organs or tissues. Yet a further object of the invention is the use of the novel chitosan derivatives as humectants for the skin or mucous membranes.

It has also surprisingly been found that the novel chitosan derivatives can be crosslinked with polyepoxides to give products which are swellable, but insoluble, in water with good mechanical properties.

The invention further relates to crosslinked chitosan derivatives obtainable by reaction of novel chitosan derivatives with at least one polyepoxide that contains on average at least two epoxy groups in the molecule.

Suitable polyepoxides are typically glycidyl compounds containing on average two epoxy groups in the molecule. Particularly suitable glycidyl compounds are those having two glycidyl groups bonded to a hetero atom (e.g. sulfur, preferably oxygen or nitrogen), β-methylglycidyl groups or 2,3-epoxycyclopentyl groups. Typical examples are preferably bis(2,3-epoxycyclopentyl) ether; diglycidyl ethers of polyhydric aliphatic alcohols, typically 1,4-butanediol, or polyalkylene glycols such as polypropylene glycols; diglycidyl ethers of cycloaliphatic polyols such as 2,2-bis(4-hydroxycyclohexyl)propane; diglycidyl ethers of polyhydric phenols such as resorcinol, bis(p-hydroxyphenyl)methane, 2,2-bis(p-hydroxyphenyl)propane (=diomethane), 2,2-bis(4'-hydroxy-3',5'-dibromophenyl)propane, 1,3-bis(p-hydroxyphenyl)ethane; bis(β-methylglycidyl) ethers of the above dihydric alcohols or dihydric phenols; diglycidyl esters of dicarboxylic acids such as phthalic acid, terephthalic acid, $\Delta_4$-tetrahydrophthalic acid and hexahydrophthalic acid, N,N-diglycidyl derivatives of primary amines and amides and heterocyclic nitrogen bases that carry two N-atoms, and N,N'-diglycidyl derivatives of disecondary diamides and diamines, including N,N-diglycidylaniline, N,N-diglycidyltoluidine, N,N-diglycidyl-p-aminophenyl methyl ether, N,N'-dimethyl-N,N'-diglycidylbis(p-aminophenyl)methane; N',N"-diglycidyl-N-phenylisocyanurate; N,N'-diglycidylethylene urea; N,N'-diglycidyl-5,5-dimethylhydantoin, N,N'-diglycidyl-5-isopropylhydantoin, N,N-methylenebis(N',N'-diglycidyl-5,5-dimethylhydantoin), 1,3-bis(N-glycidyl-5,5-dimethylhydantoin)-2-hydroxypropane; N,N'-diglycidyl-5,5-dimethyl-6-isopropyl-5,6-dihydrouracil, triglycidylisocyanurate.

Preferred epoxides are those that are soluble in strongly polar solvents and, more particularly, those that are soluble in water.

A preferred group of polyepoxides comprises glycidylated aliphatic diols and polyoxaalkylene diols, novolaks, hydantoins, aminophenols, bisphenols and aromatic diamines or cycloaliphatic epoxy compounds. Particularly preferred polyepoxides are glycidylated aliphatic diols and polyoxaalkylene diols, cresol novolaks, diglycidyl ethers of bisphenol A and bisphenol F, or mixtures thereof.

Particularly preferred are water-soluble glycidyl aliphatic diols and polyoxaalkylenediols, as the mixing with the novel chitosan derivatives can be carried out in simple manner in aqueous systems.

To prepare novel crosslinked products it is also possible to use, in addition, curing accelerators. Typical examples of curing accelerators are 3-ethyl-4-methylimidazole, triamylammonium phenolate); mono- or polyphenols (phenol, diomethane, salicylic acid); and phosphoric acid. Curing accelerators and catalysts are normally used in an amount of 0.1 to 10% by weight, based on the polyepoxide.

The amount of polyepoxide will depend mainly on the desired degree of crosslinking and the properties associated therewith. Advantageously up to 50%, preferably up to 35% and, most preferably, up to 25%, of the structural units of the novel chitosans are crosslinked.

The preparation of the crosslinked derivatives can be carried out in a manner known per se, conveniently by mixing the components together with an optional solvent or suspension agent which is then removed by heating. The mixture can be thermally crosslinked, typically by heating to 50°–200° C.

The crosslinked chitosan derivatives are particularly suitable for the preparation of water swellable and mechanically stable moulded articles, such that shaping can be combined with the preparation. It is thus possible to prepare films and foils which can be used as membranes or surgical dressings, or to make capsules or encapsulations for chemical agents, the release of which to the environment is delayed and continuous.

The following Examples illustrate the invention in more detail.

A) Preparation of intermediates

EXAMPLE A1

Reaction of a chitosan with R(−)-4-trichloromethyl-2-oxetanone a) Activation of the chitosan To activate the chitosan, a commercial product (Fluka: average molecular weight M̄~75 000, acetyl group content 4.5%) is dissolved in 5% acetic acid and undissolved constituents are removed by filtration. The product is precipitated again by addition of 2N sodium hydroxide solution to the filtrate until the pH is 8–9. The swollen white product is freed from salts by repeated centrifugation, decantation and resuspension in distilled water or by dialysis of the aqueous suspension. Afterwards the product is dried by repeated centrifugation with dioxane up to a water content of 9.8%. Titration of a lyophilised sample of this material with 0.1N HCl, taking into account the water content of 9.8%, gives a base content of 5.11 meq/g. The dioxane-containing activated polymer gel is used for most of the subsequent reactions.

b) Reaction with R(−)-4-trichloromethyl-2-oxetanone 546.2 g of the chitosan gel (25 g of chitosan=0.115 mol) are suspended in 500 ml of dry N-methylpyrrolidone (NMP) with the addition of 25 g of LiCl and the suspension is added in increments at room temperature to a solution of 58.9 g of R(−)-4-(trichloromethyl)-2-oxetanone (0.310 mol) in 1 l of NMP. The resultant suspension is stirred for 1 hour under nitrogen and excluding moisture in a sulfonation flask fitted with reflux condenser, blade stirrer and internal thermometer, then heated to 55° C. and kept at this temperature for 24 hours. After cooling, the clear gel obtained is precipitated, with efficient stirring, with 5 liters of acetone. The fine suspension is filtered over a sintered suction filter and washed free of chloride with distilled water. The product is suspended once more in methanol and again collected by filtration. A small sample is cautiously dried under vacuum and the Cl/N ratio of elemental analysis is 3.06.

EXAMPLES A2–A10

The products listed in Table 1 are prepared in accordance with Example A1. In Examples A2 and A5 R-trichloromethyl-2-oxetanone is used. In Example A3 S-trichloromethyl-2-oxetanonine and in Example A4 R,S-4-trichloromethyl-2-oxetanone is used; and in Examples A9 and A10 S-4-trichloromethyl-4-methyl-2-oxetanone is used. The solvent is dimethyl sulfoxide (DMSO) (Examples A2 to A4 100 ml, Examples A5 to A7 800 ml, Example A8 400 ml, Examples A9 and A10 200 ml). The amount of LiCl is 5 g (Examples A2 to A4), 40 g (Examples A5 to A7), 20 g (Example A8), 10 g (Examples A9 and A10). Further particulars will be found in Table 1. In Example A9 the reaction time is 32 hours at 80° C. and in Example A10 24 hours at 80° C. and 24 hours at 100° C. In the last column the content of Cl and N is given in m eq/CCl$_3$/g m eq N/g and in brackets the Cl/N ratio.

TABLE 1

| Ex. No. | Chitosan | Amount of oxetanone | Degree of subst. (%) | Cl/N content |
|---|---|---|---|---|
| A2 | 5.0 g = 0.031 mol sigma; 6.3% acetyl | 11.7 g = 0.062 mol | 92 | 8.43/2.71 (3.11) |
| A3 | 5.0 g = 0.031 mol Fluka; M̄ 2 × 10$^6$; 4.5% Acetyl | 11.7 g = 0.062 mol | 100 | 9.02/2.57 (3.5) |
| A4 | 5.0 g = 0.031 mol Fluka; M̄ 2 × 10$^6$; 4.5% acetyl | 11.7 g = 0.062 mol | 100 | 9.22/2.49 (3.7) |
| A5 | 20 g = 0.124 mol Fluka; M̄ 2 × 10$^6$; 4.5% acetyl | 47.10 g = 0.248 mol | 95 | 8.09/2.48 (3.26) |
| A6 | 20 g = 0.124 mol Fluka; M̄ 7.5 × 10$^5$; 4% acetyl | 47.10 g = 0.248 mol | 94 | 8.47/2.50 (3.38) |
| A7 | 20 g = 0.124 mol Fluka; M̄ 7 × 10$^4$; 4.3% acetyl | 47.10 g = 0.248 mol | 97 | 8.26/2.49 (3.31) |
| A8 | 10 g = 0.062 mol chitosan of Ex. A6, activated | 23.6 g = 0.124 mol | 100 | 7.95/2.57 (3.01) |
| A9 | 5.0 g = 0.031 mol | 12.6 g = 0.062 mol | 55 | 6.06/3.24 |

TABLE 1-continued

| Ex. No. | Chitosan | Amount of oxetanone | Degree of subst. (%) | Cl/N content |
|---|---|---|---|---|
| | Fluka; $\overline{M}$ 2 × 10$^6$; 4.5% acetyl | | | (1.84) |
| A10 | 5.0 g = 0.031 mol of activated chitosan acc. Ex. A1, but from dioxane lyophilised | 12.6 g = 0.062 mol | 61 | 4.94/2.99 (1.65) |

EXAMPLE A 11 a) 20 g of chitosan (Fluka, $\overline{M}$ 7.5×10$^5$) is partially degraded with 100 ml of HCl (37%) at 75° C. over 75 minutes to chitosan oligomers [A. Domard et. al., Int. J. Biol. Macromol. 11, 297 (1989)]. The mixture of oligomers obtained is neutralised to pH 8.5 with 2N NaOH and freed from salts and very low molecular constituents by ultrafiltration through a membrane with a cut-off level of 1000. After lyophilisation, a mixture of oligomers having an average degree of polymerisation of c. 6–20 is obtained.

b) 0.7 g (4.34×10$^{-3}$ mol) of the dried mixture of oligomers is suspended in 15 ml of dry DMSO together with 750 mg of LiCl and the suspension is then added, with stirring, to a solution of 1.65 g (8.64×10$^{-3}$ mol) of R,S-4-(trichloromethyl)-2-oxetanone in 15 ml of DMSO containing 750 mg of LiCl. The mixture is stirred in an atmosphere of dry nitrogen for 3 hours at room temperature and then for 10 hours at 50° C. The oligomeric reaction product is precipitated with the 10-fold amount by volume of dichloromethane. Filtration over a glass suction filter and washing off with CH$_2$Cl$_2$ and methanol until the filtrate is free from chloride, followed by vacuum drying, gives 950 mg of a brownish powdered product which has a Cl/N ratio of 1.52.

EXAMPLE A12

In accordance with the general procedure described in Example A11, 150 mg (7.59×10$^{-4}$ mol) of chitohexaose, prepared from commercially available chitohexaose hexahydrochloride (Ikara Chem. Ind. Tokyo) by neutralisation with triethylamine, are reacted in 10 ml of dry N-methylpyrrolidone with 288 mg (1.52×10$^{-3}$ mol) of R(–)-4-trichloromethyl-2-oxetanone. Yield: 246 mg (theory 266 mg) of a beige product which is saponified direct (cf. Examples B3 and B4).

EXAMPLE A13

In accordance with the general procedure described in Example A1, 2.0 g (1.24×10$^{-2}$ mol) of a chitosan product which contains 50% of amino groups and 50% of acetylamino groups (chitin 50™, Protan A/S, Norway)are reacted in N-methylpyrrolidone (80 ml) with the addition of 4 g of LiCl with 2.36 g (1.24×10$^{-2}$ mol) of R(–)-4-(trichloromethyl)-2-oxetanone. To bring the reaction to completion, the reaction mixture is stirred for 18 hours at 80° C. and for a further 8 hours at 105° C., giving 1.88 g (59% of theory) of a brownish beige powdered product which has a Cl/N ratio of 0.55, corresponding to a degree of substitution of 36.6%.

EXAMPLE A14

In acordance with the procedure described in Example A1, 5 g of chitosan are activated and the dioxane-containing gel (69.1 g) is suspended in 100 ml of DMSO in which 5 g of LiCl has been dissolved. The suspension is added under N$_2$ to a solution of 14 g (6.2×10$^{-2}$ mol) of R,S-4-trichloromethyl-β-sultone [D. Borrmann et. al., Chem. Ber. 99, 1245 (1966)] in 100 ml of dry DMSO and 5 g of LiCl and the mixture is stirred at room temperature. After 15 mutes the clear yellowish gel obtained is stirred for 12 hours at room temperature. Afterwards the reaction mixture is precipitated in 2 liters of acetone with vigorous stirring. For purification, the yellowish product is stirred twice in fresh acetone and then swollen in 200 ml of methanol and in 1 liter of water to remove LiCl. The product is filtered on a glass suction filter, washed free of chloride with water, lyophilised, and the lyophilisate is dried under 10$^{-4}$ mbar for 24 hours. Yield: 6.9 g (58% of theory) of a pale yellow polymer powder with a Cl/N ratio of 3.09 and a Cl/S ratio of 3.31 as found by elemental analysis.

EXAMPLE A15

In acordance with the general procedure described in Example A14, 2 g (1.24×10$^{-2}$ mol) of chitin 50 in 80 ml of dry DMSO containing 4 g of LiCl are reacted with 2.79 g (1.24×10$^{-2}$ mol) of trichloromethyl-β-sultone. The reaction mixture is reacted for 24 hours at 50° C. and then for 5 hours at 80° C. Yield: 2.44 g of a white polymer which has a Cl/N ratio of 1.1.

B) Preparation of the chitosan derivatives

EXAMPLE B1

The product of Example A1 is subjected, direct and moist with methanol, to saponification. This is done by suspending the product in 750 ml of water and adding a solution of 34.1 g of NaOH in 254 ml of water over 45 minutes while cooling with ice. The viscous suspension so obtained is stirred for a further 14 hours at 0°–5° C., then for another 8 hours at room temperature. Titration of the reaction mixture with 1N HCl shows that 3.2 equivalents of the base have reacted, i.e. the reaction is complete. The product solution is adjusted to pH 8.0 with 2N HCl and filtered on a glass suction filter. To remove inorganic salts, the solution is subjected to ultrafiltration and the chloride-free solution is then lyophilised. The white, water-soluble product of expanded polystyrene-like consistency is dried under a high vacuum. Yield: 29.9 g (69.5% of theory); water content 19.11% by weight; carboxyl content 3.57 m eq/g (theory 3.61).

EXAMPLE B2

To prepare the sodium salt, the calculated amount of 2N sodium hydroxide solution is added to a 3% aqueous solution of the product obtained in Example B1. The solution is dialysed and then lyophilised, giving a quantitative yield of a white highly porous product that is readily soluble in water.

EXAMPLE B3

The saponification of the product of Example A12 with 5 equivalents of NaOH in aqueous suspension according to Example B 1 gives the sodium salt of chitohexaose-hexamalamide in a yield of 135 mg (73% of theory) after the product has been freed from salts in a dialysis tube with a cut-off level of M=1000 (Spectrapor No. 6).

EXAMPLE B4

The corresponding hexacarboxylic acid is prepared from the salt of Example B3 by dissolving the sodium salt in 5 ml of water. The solution is acidified with 0.1N HCl to pH 3.0, followed by fresh dialysis as described in Example B3. Yield: 93 mg (77.5% of theory) of a slightly yellowish powder which has a carboxyl group content of 3.52 m eq/g.

EXAMPLE B5

In accordance with the general procedure described in Example A14, 10.0 g (0.062 mol) of activated chitosan (138.2 g of dioxane-containing gel) are reacted in 400 ml of dry DMSO and 16 g of LiCl with 13.7 g (0.062 mol) of 4-(diethylphosphonomethyl)-2-oxetanone (J. G. Dingwall et. al., J. Chem. Soc., Perkin Trans I 1986, p. 2081). The reaction mixture is stirred for 24 hours at 60° C. and then worked up, giving 7.5 g of a white polymer powder which has a P/N ratio of 0.72.

EXAMPLE B6

In a 100 ml sulfonation flask equipped with stirrer, reflux condenser and thermometer, 3 g (0.0145 mol) of benzyl 2-oxetanone-4-carboxylate are dissolved in 25 ml of dry dioxane. To this solution are added 2.31 g (0.0132 mol) of activated chitosan (according to Example A1; 33.1 g of dioxane-containing chitosan gel) at room temperature and the reaction mixture is stirred for 18 hours. The reaction mixture is then heated for 8 hours to 60° C. and for a further 48 hours to 100° C. The consumption of β-lactone in the reaction mixture as an indication of the progress of the reaction can be monitored by thin-layer chromatography on silica gel with toluene/ethyl acetate 1:1 as eluant. The reaction product is subsequently precipitated in 500 ml of diethyl ether, collected by filtration and washed with 3×100 ml of diethyl ether. The product is suspended in 50 ml of dioxane and then lyophilised, and the lyophilisate is dried under $10^{-2}$ mbar for 24 hours over phosphorus pentoxide. Yield: 2.85 g (58.8% of theory) of a white polymer powder which according to elemental analysis is substituted to a degree of 66.2%.

EXAMPLE B7

To remove the benzyl protective group from the product of Example B6, 2 g of the product are dissolved in 100 ml of dry tetrahydrofuran and, after addition of 40 mg of palladium acetate, hydrogenated at 50° C. and 50 bar hydrogen pressure for 21 hours. The catalyst is afterwards removed by filtration on a glass suction filter. The polymeric acid is extracted from the filter residue with 0.1N NaOH and combined with the filtrate, which is also adjusted to pH 8. After dialysis through a membrane with a cut-off level of 1000 and subsequent lyophilisation there are obtained 1.48 g (83% of theory) of a white powder which is the sodium salt of the polymeric acid. No more signals of the benzyl group can be detected in the $^1$H-NMR spectrum of the polymer in DMSO-$d_6$.

EXAMPLE B8

In accordance with the general procedure described in Example B1, the product of Example A14 is saponified with sodium hydroxide solution. This is done by adding a solution of 2.85 g (71.12×10$^{-3}$ mol) of NaOH in 23 ml of water to a suspension of 5 g (12.93×10$^{-3}$ mol) of the product in 5 ml of water and stirring the mixture for 2 hours, whereupon the suspension becomes a clear solution which is stirred for a further 12 hours at 0°–5° C. Titration of the reaction mixture with 0.1N HCl shows that 3.64 equivalents of sodium hydroxide have been consumed. For working up, the reaction mixture is freed from minor amounts of gel by filtration on a glass suction after, adjusted to pH 3.0 with 2N HCl solution while cooling with ice, and subsequently dialysed against distilled water through a membrane with an exclusion limit of 1000 Dalton. The dialysate is lyophilised and the product is dried under $10^{-2}$ mbar for 24 hours. Titration of the yellowish polymer obtained in 65.3% yield (2.61 g) with 0.1N NaOH shows a carboxyl group content of 1.67 m eq/g.

EXAMPLE B9

In accordance with the general procedure described in Example B1, 2 g of the product of Example A2 are saponified with 1.23 g of NaOH and the acid so obtained, having a carboxyl group content of 2.8 m eq/g., is isolated.

EXAMPLE B10

In accordance with the general procedure described in Example B1, 5 g of the product of Example A4 having a molecular weight of 3.40×10$^6$ are saponified with 3.12 g of NaOH and the acid so obtained, having a carboxyl group content of 3.05 m eq/g., is isolated.

EXAMPLE B11

In accordance with the general procedure described in Example B1, 5 g of the product of Example A3 having a molecular weight of 3.43×10$^6$ are saponified with 3.30 g of NaOH and the acid so obtained, having a carboxyl group content of 3.1 m eq/g., is isolated.

EXAMPLE B12

In accordance with the general procedure described in Example B1, 20 g of the product of Example A5 having a molecular weight of 3.36×10$^6$ are saponified with 12.40 g of NaOH and the acid so obtained, having a carboxyl group content of 2.5 m eq/g., is isolated.

EXAMPLE B13

In accordance with the general procedure described in Example B1, 20 g of the product of Example A6 having a molecular weight of 1.28×10$^6$ are saponified with 12.40 g of NaOH and the acid so obtained, having a carboxyl group content of 3.58 m eq/g., is isolated.

EXAMPLE B14

In accordance with the general procedure described in Example B1, 20 g of the product of Example A7 having a molecular weight of 1.28×10$^6$ are saponified with 12.40 g of NaOH and the acid so obtained, having a carboxyl group content of 3.36 m eq/g., is isolated.

EXAMPLE B15

In accordance with the general procedure described in Example B1, 24 g of the product of Example A8 having a molecular weight of 1.25×10$^6$ are saponified with 13.5 g of NaOH and the acid so obtained, having a carboxyl group content of 3.65 m eq/g.(100% of theory), is isolated.

EXAMPLE B16

In accordance with the general procedure described in Example B1, 7 g of the product of Example A9 having a molecular weight of 2.79×10$^6$ are saponified with 2.9 g of NaOH and the acid so obtained, having a carboxyl group content of 1.73 m eq/g.(50% of theory), is isolated.

EXAMPLE B17

In accordance with the general procedure described in Example B1, 0.2 g of the product of Example A13 are saponified with 0.82 ml of 1N NaOH and the acid so obtained, having a carboxyl group content of 0.98 m eq/g. (50% of theory), is isolated.

EXAMPLE B18

Crosslinking of chitosan-malamic acid with metal ions or polyamines to form hydrogels.

1 ml of a 3% aqueous solution of the following reagents is added at room temperature to a 0.5% aqueous solution (1 ml) of the sodium salt obtained in Example B2. The crosslinking is indicated by the formation of an insoluble precipitate in the form of a hydrogel:

| Salt | Consistency |
|---|---|
| aluminium acetate | white hydrogel |
| iron(III) nitrate | yellow hydrogel |
| polyethyleneimine | white hydrog |
| chitosan.CH$_3$COOH | white hydrogel |
| albumin (from beef blood) | white hydrogel |

EXAMPLE B19

Triethanolamine salt of chitosan malamic acid.

400 mg (0.00144 mol) of the product of Example B1 are dissolved at room temperature in 100 ml of distilled water and undissolved constituents are removed by filtration on a glass suction filter. Then 215 mg (0.00144 mol) of triethanolamine are added dropwise to the clear solution. The viscous solution can be applied in a thin layer (1000 μm) with a doctor blade to glass plates or polyester sheets and air dried. The thin, glass-clear films obtained bond well to glass, but can be easily removed from a polyester substrate. Lyophilization of the solution gives the triethanolamine salt of chitosan malamic acid in the form of a white, bulky powder which is readily soluble in water.

EXAMPLE B20

Crosslinking of chitosan malamic acid with diepoxides to form hydrogel films.

A solution of 0.01 ml of the diglycidyl ether of 1,4-butane diol in 1 ml of water is added at room temperature to 22 ml of a 0.3% aqueous solution of the product of Example B2. The resultant clear solution is cast to a film on a polyester substrate as described in Example B19. The film is dried to give a clear film which is crosslinked by heating for 3 hours to 100° C. and which can be hardened to a coating which is swellable, but no longer soluble, in water.

EXAMPLE B21

Preparation of a polyelectrogel.

Equimolar amounts of a 0.024 molar aqueous solution of a product of Example B2 and a 0.062 molar aqueous solution of the chitosan/acetic acid salt are mixed, with vigorous stirring. The resultant precipitate is collected by filtration, washed with water until neutral and lyophilised. The bulky polyelectrolyte powder is dried under $10^{-2}$ mbar for 24 hours. It contains solely chitosan and malic acid as components and, despite the severe drying, has a residual water content of 14.8% by weight. The product swells in water to a glass-clear and very bulky gel which is able to bind large amounts of water.

EXAMPLE B22

The solution used in Example B21 is cast to a film and placed in a solution of chitosan acetate to give a water-insoluble polyelectrolyte film. The film is glass-clear, strongly refractive and contains the 50- to 100-fold amount by volume of water. The film has a hybrid structure in which solely the polyelectrolyte gel with chitosan as polymeric counterion is formed on the surface of the primary film of chitosan-malamic acid.

Laminate films of reverse structure with similar properties, namely with chitosan as primary film and chitosan-malamic acid as polymeric counterion, are prepared by the same procedure.

C) Use Examples

EXAMPLE C1

Crystallisation of sodium chloride under the influence of acid polysaccharides

A solution of 204 g of sodium chloride in 600 ml of distilled water is filtered through a membrane filter and put into each of 6 glass beakers covered with a filter paper and provided with a blade stirrer. The stirring rate is adjusted to 30 rpm. Then to each of the 6 solutions is added 1 ml of a solution that contains 1 mg of one of the polysaccharides listed below. The concentration of polysaccharide in the crystallisation solution is thus 10 ppm. Then the solutions are stirred for 4 days at room temperature and afterwards the crystals obtained are isolated by filtration. Form, size, size distribution, agglomeration and adhesion of the crystals are assessed by microscopy and scanning electron photomicrographs. The results are reported in Table 3.

TABLE 3

| Polysaccharide | Crystal form and size | Size distribution | Adhesion |
|---|---|---|---|
| hyaluronic acid | cubes of different size, mm agglomerates irregular growth | broad range 5μ to 2 mm | growth on glass wall and stirrer |
| i-carrageenan | as above, agglomerates and cubes of mm size | broad range 5μ to 2 mm | growth on glass wall and stirrer |
| x-carrageenan | as above, agglomerates and cubes of mm size | broad range 5μ to 2 mm | growth on glass wall and stirrer |
| chondroitin-4-sulfate | round agglomerates of many single crystals, cube structure | less heterogeneous 30–300 μm | growth on glass wall and stirrer |
| chitosan-malamic acid acc. Ex. B1 | regular, well formed twin to quadruplet aggregates of octahedron structure | uniform 50–100 μm | no growth on glass parts |
| blank test | cube agglomerates of different size | broad range 5μ to 2 mm | growth on glass wall and stirrer |

EXAMPLE C2

Crystallisation of calcium carbonate under the influence of polysaccharides

A saturated solution of calcium hydrogencarbonate is prepared by suspending 700 mg of $CaCO_3$ in 700 ml of distilled water, introducing $CO_2$ until solution is almost complete, and filtration. The undissolved constituents are removed by filtration and the solution is put into each of 6 glass beakers as described in Example C1 and to each of which are added 10 ppm of the polysaccharides listed below. The solutions are heated for 1 hour to 80°–85° C. and the $CaCO_3$ precipitates are evaluated as described in Example C1.

| Polysaccharide | Crystal form and size | Size distribution | adhesion |
|---|---|---|---|
| blank test | aggregates of needles | 30–300 μm | hard crusts on some glass parts |
| hyaluronic ac | aggregates of needles | 30–300 μm | hard crusts on some glass parts |
| i-carrageenan | aggregates of needles | 30–300 μm | hard crusts on some glass parts |
| x-carrageenan | aggregates of needles | 30–300 μm | hard crusts on some glass parts |
| chondroitin-4-sulfate | growth of needles aggregates | 30–300 μm | hard crusts on some glass parts |
| chitosan-mal-amic acid acc. Ex. C1 | amorphous plates 5–10 μm thick | 30–100 μm | no crusts, all in suspension |

EXAMPLE C3 a) In accordance with the general procedure described in Example C1, solutions having the following ion concentrations are prepared:

| | |
|---|---|
| 375 ppm Ca | 220 ppm $HCO_3^\ominus$ |
| 183 ppm Mg | 85 ppm $CO_3^{2\ominus}$ |

After addition of 2 and 8 ppm respectively of a polysaccharide, the solutions are heated for 30 minutes to 70° C. and filtered after cooling. The uncrystallised calcium concentration in the filtrates is determined by atomic absorption analysis (or titration with a 0.01M solution of ethylenediaminetetraacetic acid) and expressed in percentage inhibition.

b) In similar manner, the inhibition of the barium sulfate concentration with different polysaccharides is determined by the standardised Downell test.

The test is carried out by starting from a solution which contains 8.9 ppm of $Ba^{2+}$, 20 000 ppm of NaCl and 8 ppm of a polysaccharide. The solution is adjusted with acetate buffer to pH 5.5 and kept at 25° C. Then 270.5 ppm of $SO_4^{2-}$ are added, precipitated $BaSO_4$ is removed by filtration after 4 hours and, as described in a), the residual $Ba^{2+}$ concentration in the filtrates is determined.

The results of the inhibition of crystallisation are reported in Table 4.

TABLE 4

| | | Inhibition of crystallisation (%) | |
|---|---|---|---|
| Polysaccharide | Concentration in ppm | Ca/MgCO$_3$ | BaSO$_4$ |
| i-carrageenan sodium | 8 | 10 | 0 |
| | 8 | 0 | 0 |

TABLE 4-continued

| | | Inhibition of crystallisation (%) | |
|---|---|---|---|
| Polysaccharide | Concentration in ppm | Ca/MgCO$_3$ | BaSO$_4$ |
| chondroitin-4-sulfate sodium | 8 | 0 | 0 |
| chondroitin-6-sulfate | | | |
| x-carrageenan | 8 | 8.6 | 0 |
| xanthane | 8 | 10.6 | 0 |
| polygalacturonic acid | 8 | 20 | 0 |
| alginic acid | 8 | 27.6 | 0 |
| chitosan-malamic acid acc. Ex. B2 | 2 | 14.6 | 24.8 |
| chitosan-malamic acid acc. Ex. B2 | 8 | 43.6 | 67.2 |

What is claimed is:

1. A chitosan derivative containing structural units of formulae IX and X in random distribution,

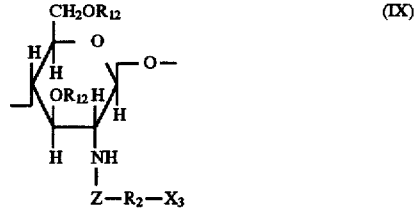

(IX)

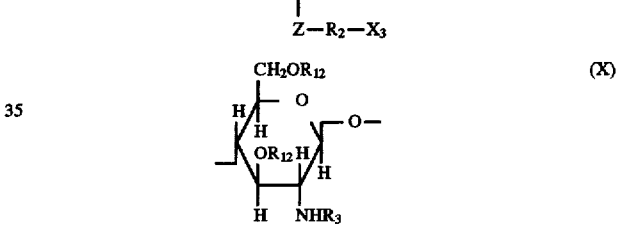

(X)

wherein the $R_{12}$ substituents are each, independently of the other, H or the radical —Z—$R_2$—$X_3$, $R_3$ is H or acetyl, Z is —CO— or —$SO_2$—, $X_3$ is —$CCl_3$, and $R_2$ is —$CHR_4CR_5$(OH)—, $R_4$ is —H, —OH, $C_1$-$C_4$alkoxy or $C_1$-$C_4$alkyl, and $R_5$ is H or $C_1$-$C_4$alkyl, which chitosan derivative contains a total of at least 2 structural units and, based on 1 mol of said chitosan derivative, 30 to 100% molar of structural units of formula IX and 70 to 0% molar of structural units of formula X.

2. A chitosan derivative according to claim 1, wherein $R_{12}$ is H.

3. A chitosan derivative according to claim 1, whereto Z is —CO—.

4. A chitosan derivative according to claim 1, wherein $R_2$ is —$CH_2CH(OH)$— or $CH_2C(CH_3)(OH)$—.

5. A chitosan derivative according to claim 1 which contains a total of at least 4 structural units.

6. An oligomeric chitosan derivative according to claim 5 which contains 4 to 50 structural units.

7. An oligomeric chitosan derivative according to claim 6 which contains 6 to 30 structural units.

8. A chitosan derivative according to claim 1 which contains 50 to 100% molar of structural units of formula IX 50 to 0% molar of structural units of formula X.

9. A chitosan derivative according to claim 1 which contains 60 to 100% molar of structural units of formula IX and 40 to 0% molar of structural units of formula X.

10. A process for the preparation of a chitosan derivative according to claim 1 containing structural units of the formulae IX and X in random distribution, which chitosan derivative contains a total of at least 2 structural units and, based on 1 mole of said chitosan derivative, 30 to 100% molar of structural units of formula IX and 70 to 0% molar of structural units of formula X, which process comprises reacting a chitosan containing a total of at least 2 structural units of the formulae IV and V,

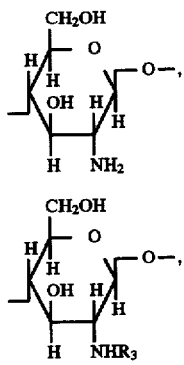

in random distribution, wherein $R_3$ is acetyl or H, and said chitosan contains 30 to 100% molar of structural units of formula IV and 70 to 0% molar of structural units of formula V based on 1 mole of chitosan, in the presence of an inert solvent, with at least 30% molar of a lactone of formula VI, based on said chitosan,

wherein $R_4$ is —H, —OH, $C_1$-$C_4$alkoxy or $C_1$-$C_4$alkyl, $R_5$ is H or $C_1$-$C_4$alkyl, $Z_1$ is =CO or =$SO_2$ and $X_1$ is —$CCl_3$.

11. A process according to claim 10, wherein the reaction is carried out in the temperature range from 0° to 150° C.

12. A process according to claim 11, wherein the reaction is carried out in the temperature range from 10° to 120° C.

13. A process according to claim 12, wherein the reaction is carried out in the temperature range from 20° to 100° C.

14. A process according to claim 10, wherein the solvent is selected from the group consisting of cyclic ethers, N-alkylated acid amides and lactams, sulfoxides and sulfones.

* * * * *